(12) United States Patent
Lee et al.

(10) Patent No.: US 11,083,374 B2
(45) Date of Patent: Aug. 10, 2021

(54) SPECTROMETER AND OPERATION METHOD OF SPECTROMETER

(71) Applicant: SAMSUNG ELECTRONICS CO., LTD., Suwon-si (KR)

(72) Inventors: Seung Jun Lee, Seoul (KR); June Young Lee, Seongnam-si (KR); Jung Mok Bae, Seoul (KR); Eui Seok Shin, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 303 days.

(21) Appl. No.: 15/616,191

(22) Filed: Jun. 7, 2017

(65) Prior Publication Data

US 2018/0125369 A1 May 10, 2018

(30) Foreign Application Priority Data

Nov. 7, 2016 (KR) .......................... 10-2016-0147603

(51) Int. Cl.
*A61B 5/00* (2006.01)
*A61B 5/145* (2006.01)
(Continued)

(52) U.S. Cl.
CPC ............ *A61B 5/0075* (2013.01); *A61B 5/103* (2013.01); *A61B 5/14532* (2013.01);
(Continued)

(58) Field of Classification Search
CPC ... A61B 5/0075; A61B 5/103; A61B 5/14532; A61B 5/44; A61B 5/441; A61B 5/6843;
(Continued)

(56) References Cited

U.S. PATENT DOCUMENTS 5,459,317 A 10/1995 Small et al.
6,167,290 A * 12/2000 Yang .................. A61B 5/14532
600/316
(Continued)

FOREIGN PATENT DOCUMENTS

JP 3566277 B1 9/2004
JP 2008104751 A 5/2008
(Continued)

OTHER PUBLICATIONS

Yongjoo Kwon, et al., "Development of Micro Variable Optics Array", MEMS 2014, San Francisco, CA, USA, Jan. 26-30, 2014, pp. 72-75.

*Primary Examiner* — Matthew Kremer
*Assistant Examiner* — Avery M Foley
(74) *Attorney, Agent, or Firm* — Sughrue Mion, PLLC

(57) ABSTRACT

A spectrometer includes a chamber, a vacuum generator configured to suck in internal air of the chamber to pull skin of a subject into the chamber, a light source configured to emit light to the skin of the subject pulled into the chamber, a photodetector configured to receive light passing through the skin of the subject and acquire a spectrum of the light; and a skin contact adjuster configured to determine a contact state between the chamber and the skin by analyzing the spectrum of the light and thereby generate a determination result, and adjust the contact state between the chamber and the skin by applying a physical force to a periphery of the skin pulled into the chamber according to the determination result.

17 Claims, 15 Drawing Sheets

(51) Int. Cl.
*A61B 5/103* (2006.01)
*G01N 21/3563* (2014.01)
*G01N 21/359* (2014.01)
*A61B 5/1455* (2006.01)

(52) U.S. Cl.
CPC ............ *A61B 5/441* (2013.01); *A61B 5/6843* (2013.01); *G01N 21/359* (2013.01); *G01N 21/3563* (2013.01); *A61B 5/1451* (2013.01); *A61B 5/1455* (2013.01); *G01N 2800/20* (2013.01)

(58) Field of Classification Search
CPC ... A61B 5/6844; A61B 5/6834; A61B 5/1451; A61B 5/1455; G01N 21/3563; G01N 21/359; G01N 2800/20
See application file for complete search history.

(56) References Cited

U.S. PATENT DOCUMENTS

| | | | |
|---|---|---|---|
| 6,954,661 | B2 | 10/2005 | Cho et al. |
| 7,315,752 | B2 * | 1/2008 | Kraemer ............ A61B 5/14532 600/310 |
| 7,771,374 | B2 | 8/2010 | Slatkine |
| 2005/0159658 | A1 | 7/2005 | Jeon et al. |
| 2006/0259102 | A1 * | 11/2006 | Slatkine ............... A61B 17/205 607/88 |
| 2007/0032747 | A1 * | 2/2007 | Hashimshony ...... A61B 5/6843 600/587 |
| 2010/0041969 | A1 | 2/2010 | Beise |
| 2014/0159862 | A1 | 6/2014 | Yang et al. |
| 2014/0316269 | A1 | 10/2014 | Zhang et al. |
| 2015/0109617 | A1 * | 4/2015 | Gilbert ............... A61B 5/14532 356/300 |
| 2016/0157733 | A1 | 6/2016 | Gil |
| 2016/0157752 | A1 | 6/2016 | Cho et al. |
| 2017/0143209 | A1 | 5/2017 | Lee et al. |
| 2018/0098708 | A1 * | 4/2018 | Lee .......................... A61B 5/00 |

FOREIGN PATENT DOCUMENTS

| | | |
|---|---|---|
| JP | 5684443 B2 | 3/2015 |
| KR | 100634500 B1 | 10/2006 |
| KR | 100775669 B1 | 11/2007 |
| KR | 101491854 B1 | 2/2015 |
| KR | 101512076 B1 | 4/2015 |
| KR | 1020160050399 A | 5/2016 |

* cited by examiner

SPECTROMETER AND OPERATION METHOD OF SPECTROMETER

CROSS-REFERENCE TO RELATED APPLICATION(S)

This application claims priority under 35 USC § 119(a) to Korean Patent Application No. 10-2016-0147603, filed on Nov. 7, 2016, in the Korean Intellectual Property Office, the entire disclosure of which is incorporated herein by reference for all purposes.

BACKGROUND

1. Field

Methods and apparatuses consistent with exemplary embodiments disclosed herein relate to a spectrometer and an operation method of the spectrometer.

2. Description of Related Art

Studies on measuring and analyzing biological components in the skin using a non-invasive method which uses a near infrared (NIR) spectrometer have attracted much attention. Most studies use a transmission mode or a reflection mode to measure skin spectrum. Here, the transmission mode uses a large magnitude of a signal, which is limited in the position of the skin where it can be applied, since the signal has to be transmitted through the skin. The reflection mode is the most ideal mode for application on a system for measuring a skin spectrum, but the magnitude of a signal is very small due to the scattering characteristic of the skin. A trade-off between these two modes is a transflectance mode.

In the transflectance mode, an NIR spectrometer pulls the skin into a chamber to stably secure the skin, then emits light to the skin, and acquires a skin spectrum by receiving light irradiated from the skin.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to an aspect of an exemplary embodiment, there is provided a spectrometer including: a chamber; a vacuum generator configured to suck in internal air of the chamber to pull skin of a subject into the chamber; a light source configured to emit light to the skin of the subject pulled into the chamber; a photodetector configured to receive the light passing through the skin of the subject and acquire a spectrum of the light; and a skin contact adjuster configured to determine a contact state between the chamber and the skin by analyzing the spectrum of the light and thereby generate a determination result, and adjust the contact state between the chamber and the skin by applying a physical force to a periphery of the skin pulled into the chamber according to the determination result.

The skin contact adjuster may be configured to determine light leakage amplitude at a specific wavelength based on the spectrum of the light and determine the contact state between the chamber and the skin based on the light leakage amplitude at the specific wavelength.

The skin contact adjuster may be configured to determine that the contact state between the chamber and the skin is inadequate, in response to the light leakage amplitude at the specific wavelength being equal to or greater than a predetermined threshold, and adjust the contact state between the chamber and the skin by applying the physical force to the periphery of the skin pulled into the chamber.

The skin contact adjuster may be configured to apply the physical force to the periphery of the skin pulled into the chamber by vertically pressing around the skin pulled into the chamber or oscillating back and forth or side to side around the skin pulled into the chamber.

The skin contact adjuster may be configured to adjust the physical force around the skin pulled into the chamber according to light leakage amplitude at a specific wavelength which is determined based on the spectrum of the light.

The spectrometer may further include a light path adjuster configured to calculate an effective light path length of the light and adjust a propagation path of light to be emitted to the skin from the light source based on the calculated effective light path length.

The light path adjuster may be configured to calculate the effective light path length by analyzing the spectrum of the light using a classical least square (CLS) algorithm.

The light path adjuster may be configured to adjust the propagation path of the light using two liquids which form a continuous refractive interface and are not mixed with each other.

The light path adjuster may include: a container; two liquids inside of the container which form an interface with each other and are not mixed with each other; and a plurality of electrodes which induce an electric field of a predetermined magnitude inside the container so that a direction of the interface is changed.

One of the two liquids may be a conductive liquid and the other liquid may be an insulating liquid.

According to an aspect of another exemplary embodiment, there is provided a method of operating a spectrometer, the method including: pulling skin of a subject into a chamber by sucking in internal air of the chamber; emitting light to the skin of the subject pulled into the chamber; receiving the light passing through the skin of the subject and acquiring a spectrum of the light; determining a contact state between the chamber and the skin by analyzing the spectrum of the light and thereby generating a determination result; and adjusting the contact state between the chamber and the skin by applying a physical force to a periphery of the skin of the subject pulled into the chamber according to the determination result.

The determining of the contact state between the chamber and the skin may include determining light leakage amplitude at a specific wavelength based on the spectrum of the light and determining the contact state between the chamber and the skin based on the light leakage amplitude at the specific wavelength.

The determining of the contact state between the chamber and the skin may include determining that the contact state between the chamber and the skin is inadequate, in response to the light leakage amplitude at the specific wavelength being equal to or greater than a predetermined threshold.

The adjusting of the contact state between the chamber and the skin may include applying the physical force to the periphery of the skin pulled into the chamber by vertically pressing around the skin pulled into the chamber or oscillating back and forth or side to side around the skin pulled into the chamber.

The adjusting of the contact state between the chamber and the skin may include adjusting the physical force around the skin pulled into the chamber according to light leakage amplitude at a specific wavelength which is determined based on the spectrum of the light.

The method may further include: calculating an effective light path length of the light; and adjusting a propagation path of light to be emitted to the skin from a light source based on the calculated effective light path length.

The calculating of the effective light path length of the light may include calculating the effective light path length by analyzing the spectrum of the light using a classical least square (CLS) algorithm.

The adjusting of the propagation path of the light may include adjusting the propagation path of the light using two liquids which form a continuous refractive interface and are not mixed with each other.

One of the two liquids may be a conductive liquid and the other liquid may be an insulating liquid.

Other features and aspects will be apparent from the following detailed description, the drawings, and the claims.

Figure 1:
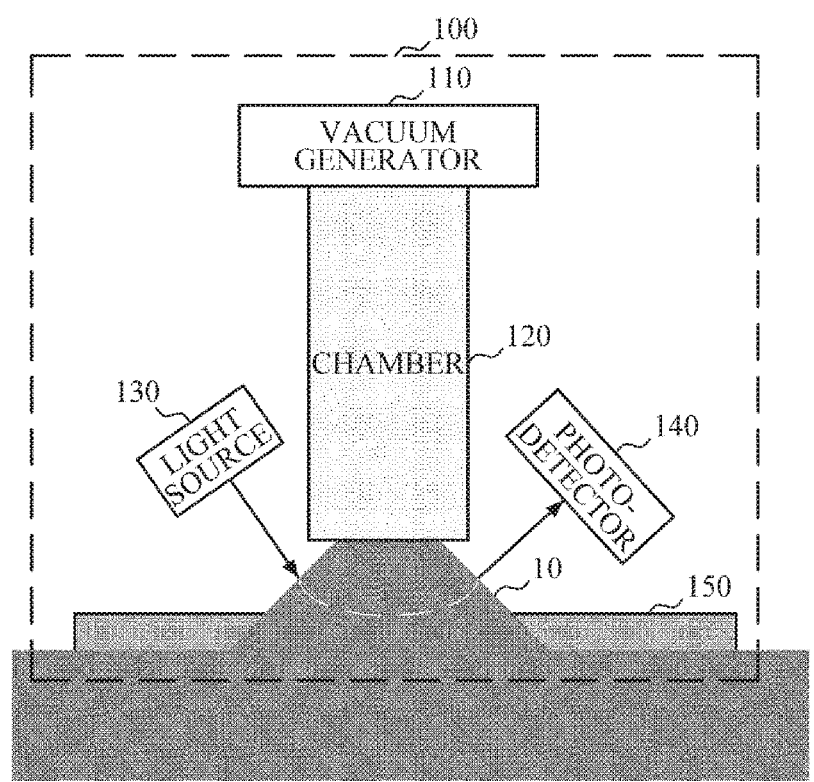
FIG. 1 is a block diagram illustrating an exemplary embodiment of a spectrometer.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses and/or systems described herein. Various changes, modifications, and equivalents of the systems, apparatuses and/or methods described herein will suggest themselves to those of ordinary skill in the art. In the following description, a detailed description of known functions and configurations incorporated herein will be omitted when it may obscure the subject matter with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described below are selected by considering functions in the exemplary embodiment and meanings may vary depending on, for example, a user or operator's intentions or customs. Therefore, in the following exemplary embodiments, when terms are specifically defined, the meanings of terms should be interpreted based on definitions, and otherwise, should be interpreted based on general meanings recognized by those skilled in the art.

As used herein, the singular forms are intended to include the plural forms as well, unless the context clearly indicates otherwise. It will be further understood that the terms "comprises" and/or "comprising," or "includes" and/or "including" when used in this description, specify the presence of stated features, numbers, steps, operations, elements, components or combinations thereof, but do not preclude the presence or addition of one or more other features, numbers, steps, operations, elements, components or combinations thereof.

It will also be understood that the elements or components in the following description are discriminated in accordance with their respective main functions. In other words, two or more elements may be made into one element or one element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

FIG. 1 is a block diagram illustrating an exemplary embodiment of a spectrometer.

Referring to FIG. 1, the spectrometer 100 includes a vacuum generator 110, a chamber 120, a light source 130, a photodetector 140, and a skin contact adjuster 150.

The vacuum generator 110 may suck in the internal air of the chamber 120 to maintain a vacuum in the chamber 120 so that the skin 10 of a subject is pulled into the chamber 120.

The light source 130 emits light to the skin 10 of the subject. For example, the light source 130 may emit light of a specific wavelength, for example, near infrared (NIR) light to the skin 10. However, the wavelength of the light to be emitted from the light source 130 may vary according to the purpose of measurement or the types of component to be measured. In addition, the light source 130 is not necessarily formed with a single illuminator, and may be formed by a group of a plurality of illuminators. In the case where the light source 130 is formed by a group of a plurality of illuminators, the illuminators may emit light of different wavelengths to achieve the purpose of measurement, or all the illuminators may emit light of the same wavelength. The illuminator may include a light emitting diode (LED), a laser diode, or the like.

The photodetector 140 receives transmitted light passing through the skin 10 from among the light emitted from the light source 130, and acquires a spectrum of the received light. According to an exemplary embodiment, the photodetector 140 may include a photodiode, a photo transistor (PTr), or a charge-coupled device (CCD). The photodetector 140 is not necessarily formed with a signal element, and may be formed as an array of a plurality of elements.

Meanwhile, the spectrum of the light acquired by the photodetector 140 contains information on the interior of the subject, and hence the spectrum of the light may be utilized in analyzing the constituent elements inside the subject, such as blood sugar.

The skin contact adjuster 150 determines a contact state between the chamber 120 and the skin 10.

The contact state between the skin of the subject and the chamber 12 affects the quality of the transmitted light used for analyzing the constituent elements inside the subject. That is, when the skin 10 of the subject is gathered to one side of the chamber 120 and is brought into contact with the chamber 120, the quality of the transmitted light passing through the skin 10 is lowered, and consequently, the analysis of constituent elements inside the subject is inaccurate. Therefore, the contact state between the skin 10 of the subject and the chamber 120 needs to be adjusted such that the skin 10 of the subject makes uniform contact with the chamber 120 without being gathered to one side of the chamber 120.

According to an exemplary embodiment, the skin contact adjuster 150 may analyze the spectrum of the acquired transmitted light and determine the contact state between the chamber 120 and the skin 10. For example, the skin contact adjuster 150 may determine light leakage amplitude at a specific wavelength on the basis of the spectrum of the acquired transmitted light, and, when the light leakage amplitude is equal to or greater than a predetermined threshold, may determine that the contact state between the chamber 120 and the skin 10 is inadequate. In this case, the specific wavelength may be a wavelength that reacts with water, e.g., a wavelength to be absorbed by water, and may be set variously according to the purpose of measurement or a type of constituent element to be measured.

When the contact state between the chamber 120 and the skin 10 is determined to be inadequate, the skin contact adjuster 150 may adjust the contact state between the chamber 120 and the skin 10. According to an exemplary embodiment, the skin contact adjuster 150 may adjust the contact state between the chamber 120 and the skin 10 by applying a physical force around the skin 10 pulled into the chamber 120. For example, when it is determined that the contact state between the chamber 120 and the skin 10 is inadequate, the skin contact adjuster 150 may apply a physical force around the skin 10 of the subject pulled into the chamber 120 by vertically pressing the periphery of the skin 10 pulled into the chamber 120 or oscillating back and forth or side to side around the skin 10 pulled into the chamber 120. When the physical force is applied around the skin 10 of the subject pulled into the chamber 120, the process of the chamber 120 and the skin 10 of the subject contacting and separating from each other is repeated, and thereby the contact state between the chamber 120 and the skin 10 may be adjusted.

The skin contact adjuster 150 may adjust an amount of physical force applied around the skin 10 pulled into the chamber 120 according to the light leakage amplitude at a specific wavelength. For example, the skin contact adjuster 150 may classify the vertical force pressing the periphery of the skin 10 of the subject pulsed into the chamber 120 into a number of levels according to the magnitude of the force, and may divide the force that oscillates back and forth or side to side around the skin 10 of the subject pulled into the chamber 120 into a number of levels according to the magnitude of the force. In addition, the skin contact adjuster 150 may appropriately adjust the magnitude of the force pressing the periphery of the skin 10 of the subject pulled into the chamber 120 and/or the magnitude of the force oscillating back and forth or side to side around the skin 10 of the subject pulled into the chamber 120 by applying the force of a specific level corresponding to the contact state (e.g., light leakage amplitude) between the chamber 120 and the skin 10.

Figure 2A:
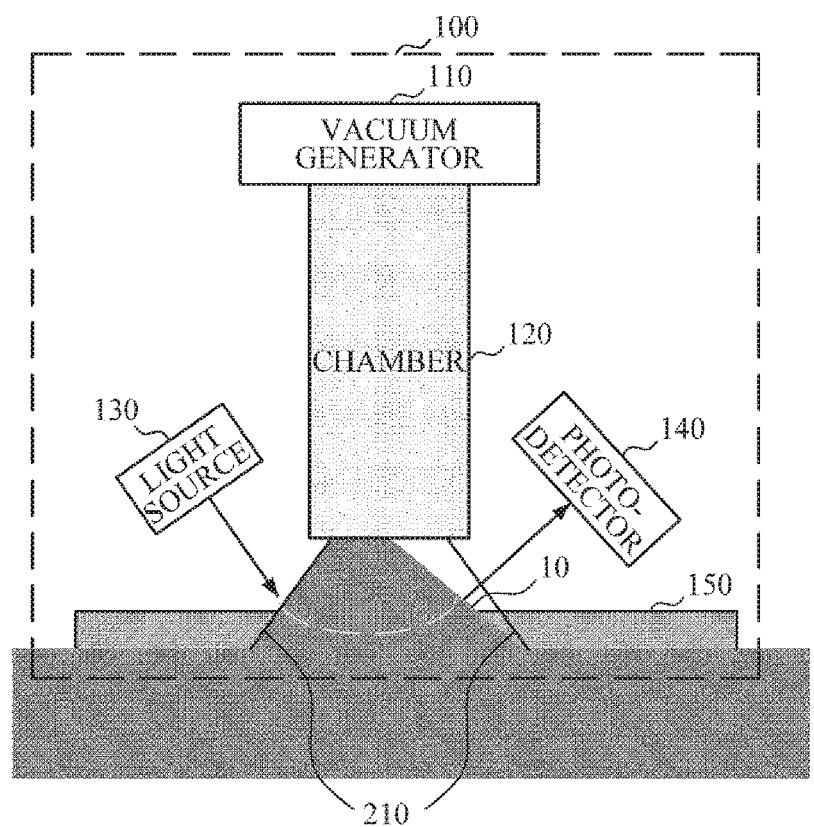
FIGS. 2A, 2B, and 2C are diagrams for describing a method of adjusting a skin contact.
Figure 2B:
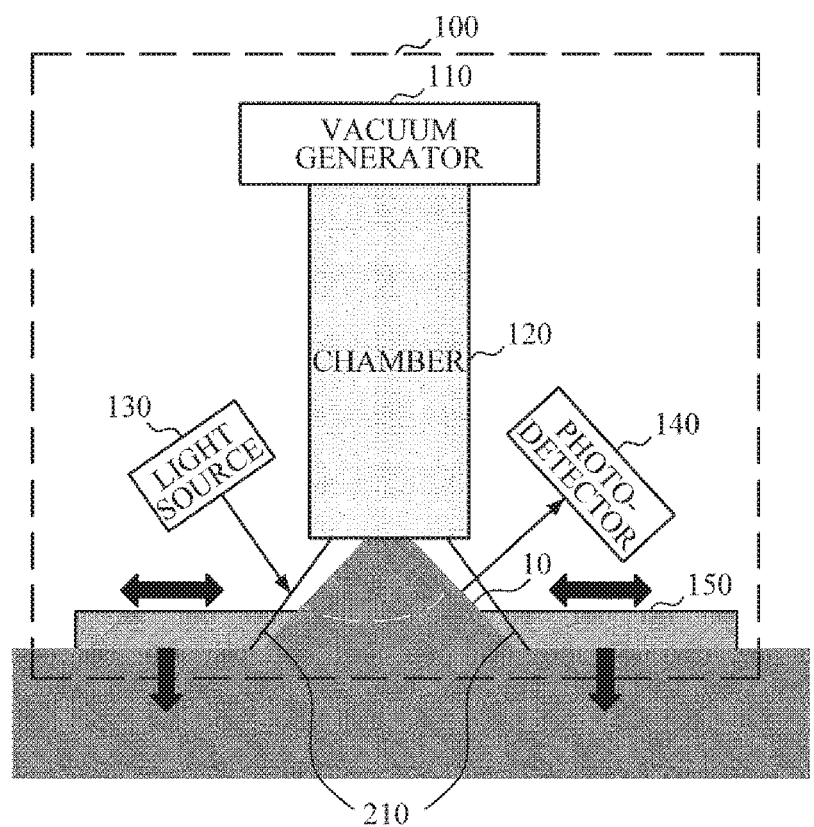
Figure 2C:
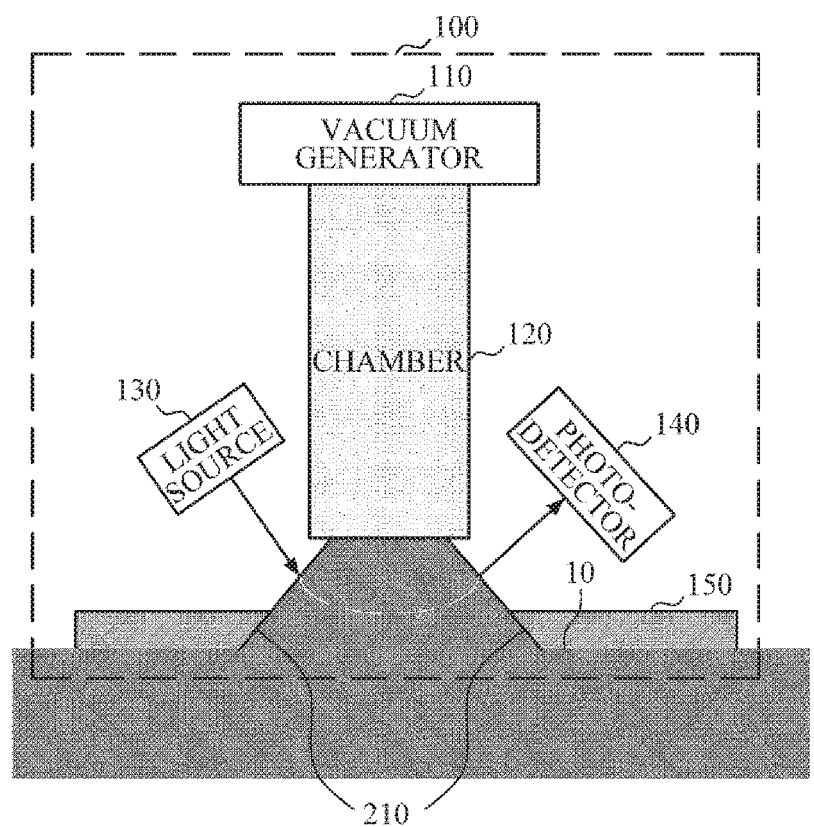

FIGS. 2A to 2C are diagrams for describing a method of adjusting skin contact. Reference numeral 210 is shown for convenience of description, which denotes a plane on which the pulled skin 10 of the subject is positioned when the chamber 120 and the skin 10 are in uniform contact with each other without deviation.

Referring to FIG. 2A, a vacuum generator 110 pulls the skin 10 of the subject into a chamber 120 by maintaining a vacuum in the chamber 120. At this time, the skin 10 of the subject is gathered to one side of the chamber 120 and is brought into non-uniform contact with the chamber 120. A light source 130 emits light to the skin 10 of the subject, and a photodetector 140 receives transmitted light passing through the skin 10 and acquires a spectrum of the received light. A skin contact adjuster 150 analyzes the acquired spectrum of the transmitted light and determines that a contact state between the chamber 120 and the skin 10 of the subject is inadequate.

Referring to FIG. 2B, the skin contact adjuster 150 applies a physical force around the skin 10 of the subject pulled into the chamber 120 by vertically pressing the periphery of the skin 10 or oscillating back and forth or side to side around the skin 10 of the subject. The process of the chamber 120 and the skin 10 of the subject pulled into the chamber 120 contacting and separating from each other is repeated according to the physical force applied around the skin 10 of the subject. The skin contact adjuster 150 may control the magnitude of force that vertically presses the periphery of the skin 10 of the subject pulled into the chamber 120 and/or the magnitude of force that oscillates back and forth/side to side around the skin 10 of the subject pulled into the chamber 120 according to the contact state between the chamber 120 and the skin 10 (e.g., the light leakage amplitude at a specific wavelength).

Referring to FIG. 2C, the skin contact adjuster 150 removes the force applied around the skin 10 of the subject pulled into the chamber 120 after a predetermined period of time. The light source 130 emits light to the skin 10 of the subject again, and the photodetector 140 receives transmitted light passing through the skin 10 and acquires a spectrum of the received light. The skin contact adjuster 150 analyzes the spectrum of the transmitted light acquired by the photodetector 140 and determines that the contact state between the chamber 120 and the skin 10 of the subject is adequate. The process of the chamber 120 and the skin 10 of the subject pulled into the chamber 120 contacting and separating from each other is repeated according to the physical force applied around the skin 10 of the subject, and consequently the chamber 120 and the skin 10 are brought into uniform contact with each other without deviation.

Figure 3A:
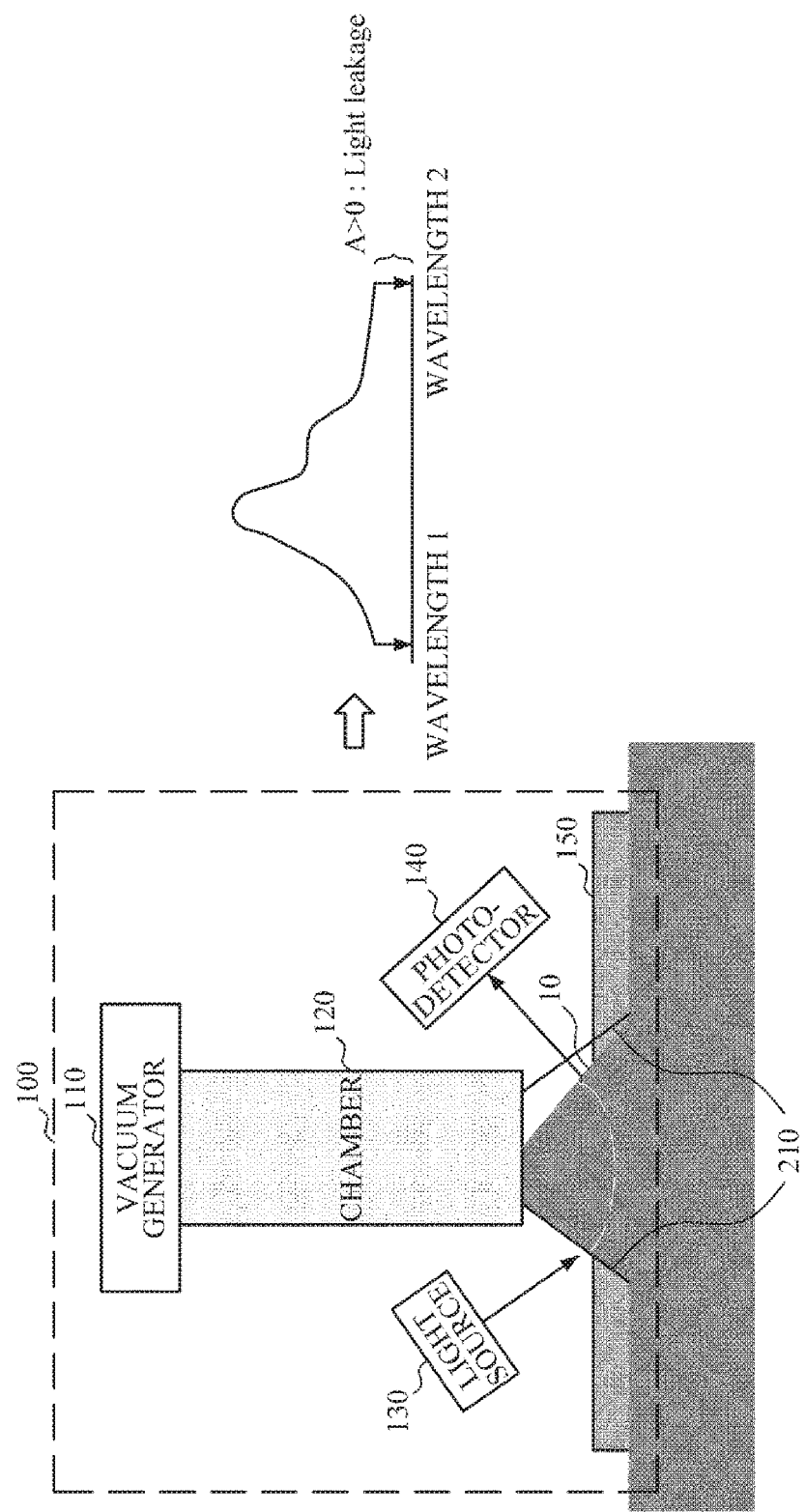
FIGS. 3A and 3B are diagrams for describing changes in a spectrum according to a contact state between a chamber and skin of a subject.
Figure 3B:
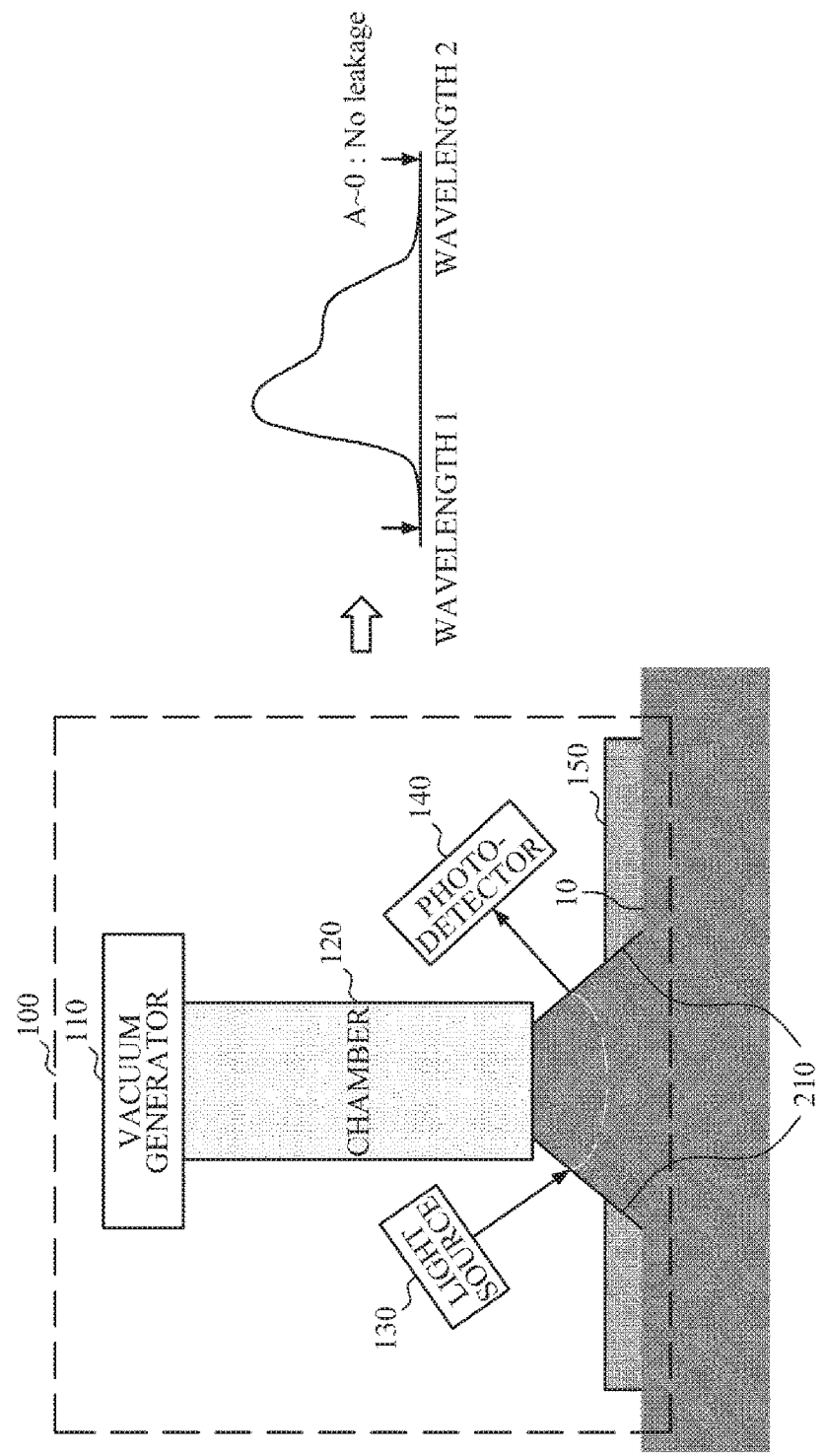

FIGS. 3A and 3B are diagrams for describing changes in spectrum according to the contact state between the chamber 120 and the skin 10 of the subject. More specifically, FIG. 3A is a diagram for describing a case of an inadequate contact state between the chamber 120 and the skin 10 of the subject, and FIG. 3B is a diagram for describing a case of an adequate contact state between the chamber 120 and the skin 10 of the subject.

Referring to FIG. 3A, in the case where the contact state between the chamber 120 and the skin 10 of the subject is inadequate, that is, where the skin 10 of the subject is gathered to one side of the chamber 120 and is brought into contact with the chamber 120, a spectrum of the transmitted light acquired by the photodetector 140 has an intensity at a specific wavelength (wavelength 1 or wavelength 2) greater than 0. That is, it is seen that light leakage occurs at the specific wavelength when the contact state between the chamber 120 and the skin 10 of the subject is inadequate.

Referring to FIG. 3B, in the case where the contact state between the chamber 120 and the skin 10 of the subject is adequate, that is, where the skin 10 of the subject is in uniform contact with the chamber 120 without being gathered to one side of the chamber 120, a spectrum of the transmitted light acquired by the photodetector 140 has an intensity at a specific wavelength (wavelength 1 or wavelength 2) equal to or close to 0. Thus, it is seen that light leakage hardly occurs at the specific wavelength when the contact state between the chamber 120 and the skin 10 of the subject is adequate.

On the basis of the relationship between the contact state between the chamber 120 and the skin 10 of the subject and the spectrum, the skin contact adjuster 150 may determine the contact state between the chamber 120 and the skin 10 of the subject. That is, the skin contact adjuster 150 may determine the light leakage amplitude at the specific wavelength by analyzing the spectrum of the transmitted light acquired by the photodetector 140. When the light leakage amplitude at the specific wavelength is equal to or greater than a predetermined threshold, the skin contact adjuster 150 may determine that the contact state between the chamber 120 and the skin 10 is inadequate.

Figure 4:
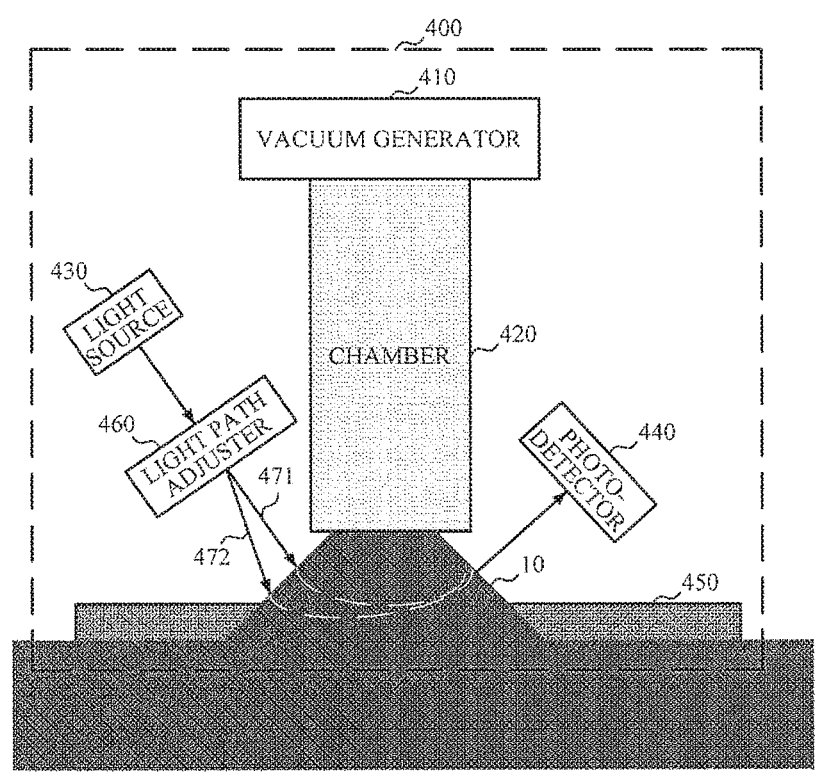
FIG. 4 is a block diagram illustrating another exemplary embodiment of a spectrometer.

FIG. 4 is a block diagram illustrating another exemplary embodiment of a spectrometer.

Referring to FIG. 4, the spectrometer 400 includes a vacuum generator 410, a chamber 420, a light source 430, a photodetector 440, a skin contact adjuster 450, and a light path adjuster 460. The vacuum generator 410, the chamber 420, the light source 430, the photodetector 440, and the skin contact adjuster of FIG. 4 are the same as the vacuum generator 110, the chamber 120, the light source 130, the photodetector 140, and the skin contact adjuster 150 of FIG. 1, and thus detailed descriptions thereof will be omitted.

The light path adjuster 460 calculates an effective light path length of transmitted light received by the photodetector 440. The effective light path length refers to a length of light passing through the water element of skin of the subject. According to an exemplary embodiment, the light path adjuster 460 may calculate the effective light path length by analyzing the spectrum of the transmitted light acquired by the photodetector 440 using a classical least square (CLS) algorithm. However, this is merely an exemplary embodiment, and aspects of the present disclosure are not limited thereto. That is, the light path adjuster 460 may calculate the effective light path length using various well-known methods.

The light path adjuster 460 adjusts a propagation path of light emitted to the skin 10 from the light source 430 on the basis of the calculated effective light path length. For example, the light path adjuster 460 may determine whether the calculated effective light path length is identical with a predetermined target effective light path length, and may adjust the propagation path of light emitted to the skin 10 from the light source 430 when the two effective light path lengths are not the same. Thus, according to whether or not the calculated effective light path length is identical with the predetermined target effective light path length, the light path adjuster 460 may change the propagation path of light which is emitted from the light source 430 in a constant direction and is incident on the skin 10. For example, the light path adjuster 460 may change a direction of the propagation path of light emitted from the light source 430 from a first direction 471 to a second direction 472 when the calculated effective light path length is smaller than the predetermined target effective light path length.

Meanwhile, a method of implementing the light path adjuster 460 is not particularly limited to the above example as long as a propagation path of light emitted from the light source 430 can be adjusted. For instance, the light path adjuster 460 may change the propagation direction of light emitted from the light source 430 by refracting the light at a predetermined angle using an optical device 500, which will be described with reference to FIG. 5. Alternatively, the light path adjuster 460 may change the propagation direction of light using a reflector capable of adjusting an angle of reflection, a combination of the reflector and the optical device 500, or a driving device capable of operating the reflector (e.g., by changing an angle of reflection of the reflector) or the combination of the reflector and the optical device 500. In addition, the light path adjuster 460 may change the propagation path of light using a refraction device having a predetermined angle of refraction and an adjustment device capable of adjusting the refraction device (e.g., by axially rotating the refraction device) to change a direction of refraction by the refraction device.

Hereinafter, an exemplary embodiment of the light path adjuster 460 will be described in detail with reference to FIG. 5.

Figure 5:
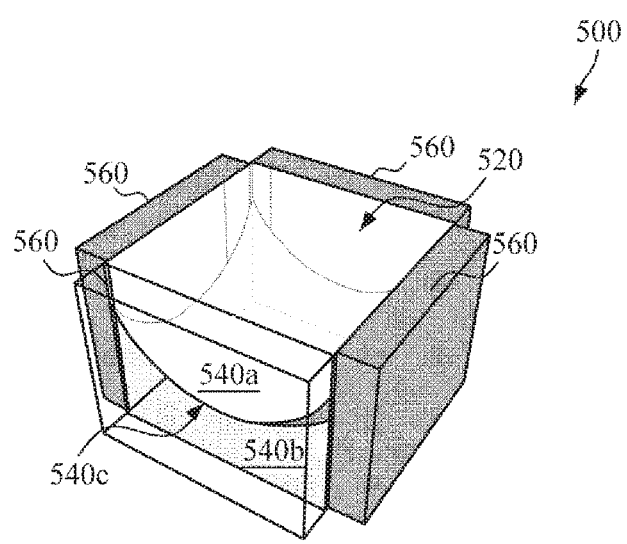
FIG. 5 is a diagram illustrating an exemplary embodiment of an optical device included in a light path adjuster.

FIG. 5 is a diagram illustrating an exemplary embodiment of an optical device included in the light path adjuster 460. The optical device 500 may change a propagation path of light by altering a refraction angle of light.

Referring to FIG. 5, the optical device 500 may include a container 520, two liquids 540a and 540b, and electrodes 560. The light path adjuster 460 may include a single optical device 500 or an array of a plurality of optical devices 500.

The container 520 contains the two liquids 540a and 540b, and may be formed of a transparent material, or at least one surface (e.g., an upper surface and a lower surface in FIG. 5) where light is input and output and which is made of a transparent material. The inner surfaces of the container 520, that is, the surfaces (at least four inner side surfaces) in contact with the two liquids 540a and 540b, may be coated with a single layer or a multi-layer formed of a dielectric material in order to use an electro-wetting property. The dielectric material may be Teflon, parylene, silicon nitride ($SiN_x$), or the like, but is not limited thereto.

One of the two liquids 540a and 540b is a conductive liquid, and the other is an insulating liquid. For example, a first liquid 540a positioned above a second liquid 540b may be a conductive liquid, and the second liquid 540b positioned below may be an insulating liquid. However, these are merely examples, and it is apparent that the electrical characteristics of the two liquids 540a and 540b may be reversed.

The conductive liquid may be pure water or water containing a predetermined electrolyte. However, aspects of the present description are not limited thereto, and types of liquids used as the conductive liquid and the insulating liquids are not particularly limited. However, it may be more useful if the conductive liquid is a liquid whose degree of spreadability can be precisely controlled using the electro-wetting property, which will be described below.

The two liquids 540a and 540b are not mixed with each other. Thus, there is an interface 540c between the two liquids 540a and 540b contained in the container 520. In addition, the direction of the interface 540c may vary according to the shape of the container 520. Light may pass through the liquid or be refracted at a predetermined angle according to the direction of the interface 540c relative to the direction in which the light is incident into the liquid, and hence the interface 540c may act as a refraction surface of the light.

The plurality of electrodes 560 are disposed on outer surfaces of the container 520. The plurality of electrodes 560 may be two or more electrodes and configured to independently apply a voltage. In FIG. 5, it is illustrated that four electrodes 560 are disposed at each side wall of the container 520 shaped as a hexahedron, which is merely an example, and more electrodes may be provided, or electrodes may be additionally disposed at other positions in addition to the side walls.

The plurality of electrodes 560 may act as a driving device for using the electro-wetting property of the conductive liquid 540a among the two liquids 540a and 540. When a predetermined voltage is applied to each of the electrodes 560 and consequently an electric field is formed inside the container 520, the spreadability of the conductive liquid 540a relative to the dielectric film, that is, the inner walls of the container 520, is changed according to the electro-wetting property. In addition, the degree of change in spreadability and a direction of change may be controlled by varying the intensity or direction of the applied voltage.

As such, when the spreadability of the conductive liquid 540a is changed, a region where the conductive liquid 540a is distributed is changed so that the areas that are occupied by each of the liquids 540a and 540b in the container 520 are also changed. Accordingly, the direction of the interface 540c between the two liquids 540a and 540b may be changed. Thus, it is possible to change the direction of the interface 540c by adjusting the voltages applied to the electrodes 560. In addition, the interface 540c may be formed as a continuous refractive interface for light by precisely controlling the change of direction of the interface 540c.

Figure 6A:
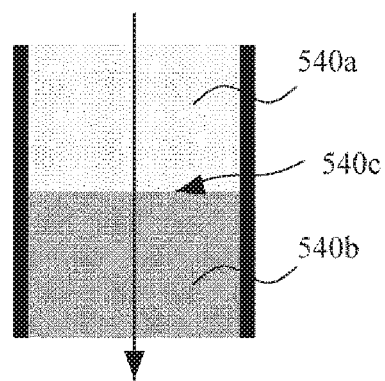
FIGS. 6A, 6B, and 6C are diagrams for describing a principle of controlling an angle of refraction of light using an optical device.
Figure 6B:
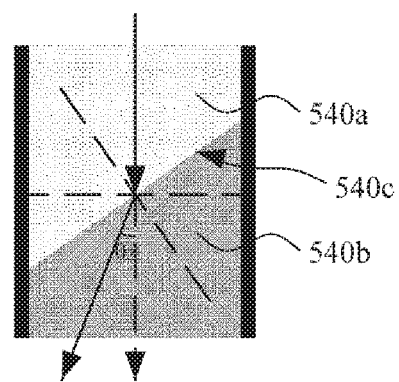
Figure 6C:
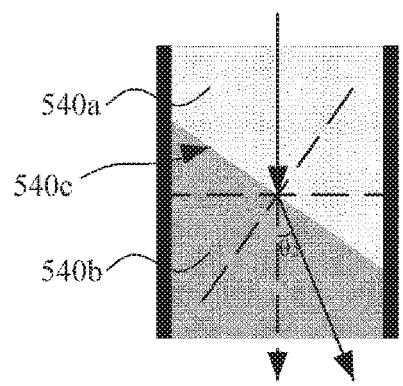

FIGS. 6A to 6C are diagrams for describing a principle of controlling an angle of refraction of light using an optical device 500. Referring to FIGS. 6A to 6C, it is seen that interfaces 540c are different from one another, which is caused by an electro-wetting property of a conductive liquid 540a due to the change in magnitude and/or direction of the electric field formed inside a container, as described above.

Referring to FIG. 6A, incident light goes straight without being refracted on the interface 540c in the horizontal direction. Referring to FIG. 6B, as the direction of the interface 540c is changed to be inclined in the upper right direction, the incident light is refracted to the left by a predetermined angle $\theta_3$. In addition, referring to FIG. 6C, as the direction of the interface 540c is changed to be included in the upper left direction, the incident light is refracted to the right by a predetermined angle $\theta_2$.

Figure 7:
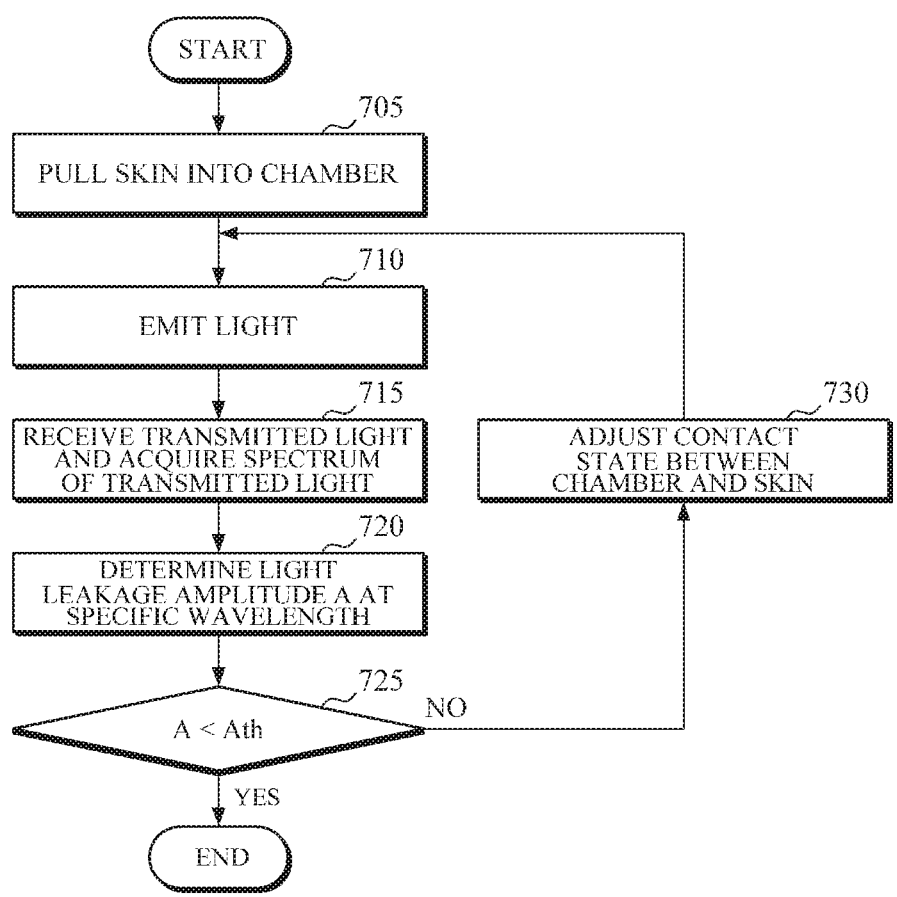
FIG. 7 is a flowchart illustrating an exemplary embodiment of a method of adjusting a skin contact state of a spectrometer.

FIG. 7 is a flowchart illustrating an exemplary embodiment of a method of adjusting a skin contact state of a spectrometer. The method of adjusting a skin contact state of FIG. 7 may be performed by the spectrometer 100 of FIG. 1.

Referring to FIGS. 1 and 7, the spectrometer 100 sucks in the internal air of the chamber 120 so that the skin 10 of the subject is pulled into the chamber 120, in operation 705.

The spectrometer 100 emits light to the skin 10 of the subject, in operation 710. For example, the spectrometer 100 may emit light of a specific wavelength, for example, NIR light to the skin 10. However, the wavelength of the light to be emitted from the spectrometer 100 may vary according to the purpose of measurement or the types of component to be measured.

The spectrometer 100 receives transmitted light passing through the skin 10 and acquires a spectrum of the received light, in operation 715.

The spectrometer 100 determines light leakage amplitude A at a specific wavelength by analyzing the spectrum of the transmitted light, in operation 720, and compares the light leakage amplitude A with a predetermined threshold Ath, in operation 725. In this case, the specific wavelength may be a wavelength that reacts with water, e.g., a wavelength to be absorbed by water, and may be set to various wavelengths according to the purpose of measurement or a type of constituent element to be measured.

When it is determined that the light leakage amplitude A at the specific wavelength is equal to or greater than the predetermined threshold Ath, the spectrometer 100 determines that the contact state between the chamber 120 and the skin 10 is inadequate and adjusts the contact state between the chamber 120 and the skin 10, in operation 730. According to an exemplary embodiment, the spectrometer 100 may adjust the contact state between the chamber 120 and the skin 10 by applying a physical force around the skin 10 pulled into the chamber 120. For example, when it is determined that the light leakage amplitude A at the specific wavelength is equal to or greater than the predetermined threshold Ath, the spectrometer 100 may apply a physical force around the skin 10 of the subject pulled into the chamber 120 by vertically pressing the periphery of the skin 10 pulled into the chamber 120 or oscillating back and forth or side to side around the skin 10 pulled into the chamber 120. When the physical force is applied around the skin 10 of the subject pulled into the chamber 120, the process of the chamber 120 and the skin 10 of the subject contacting and separating from each is repeated, and thereby the contact state between the chamber 120 and the skin 10 may be adjusted.

The spectrometer 100 may adjust the physical force around the skin 10 pulled into the chamber 120 according to the light leakage amplitude at a specific wavelength. For example, the spectrometer 100 may classify the vertical force pressing the periphery of the skin 10 of the subject pulsed into the chamber 120 into a number of levels according to the magnitude of the force, and may divide the force that oscillates back and forth/side to side around the skin 10 of the subject pulled into the chamber 120 into a number of levels according to the magnitude of the force. In addition, the spectrometer 100 may appropriately adjust the magnitude of the force pressing the periphery of the skin 10 of the subject pulled into the chamber 120 and/or the magnitude of the force oscillating back and forth or side to side around the skin 10 of the subject pulled into the chamber 120 by applying the force of a specific level corresponding to the contact state (e.g., light leakage amplitude) between the chamber 120 and the skin 10.

When the contact state between the chamber 120 and the skin 10 is adjusted, the spectrometer 100 returns to operation 710 to emit light to the skin 10. That is, the spectrometer 100 repeats operations 710, 715, 720, 725, and 730 until the light leakage amplitude A at the specific wavelength is less than the predetermined threshold Ath.

Figure 8:
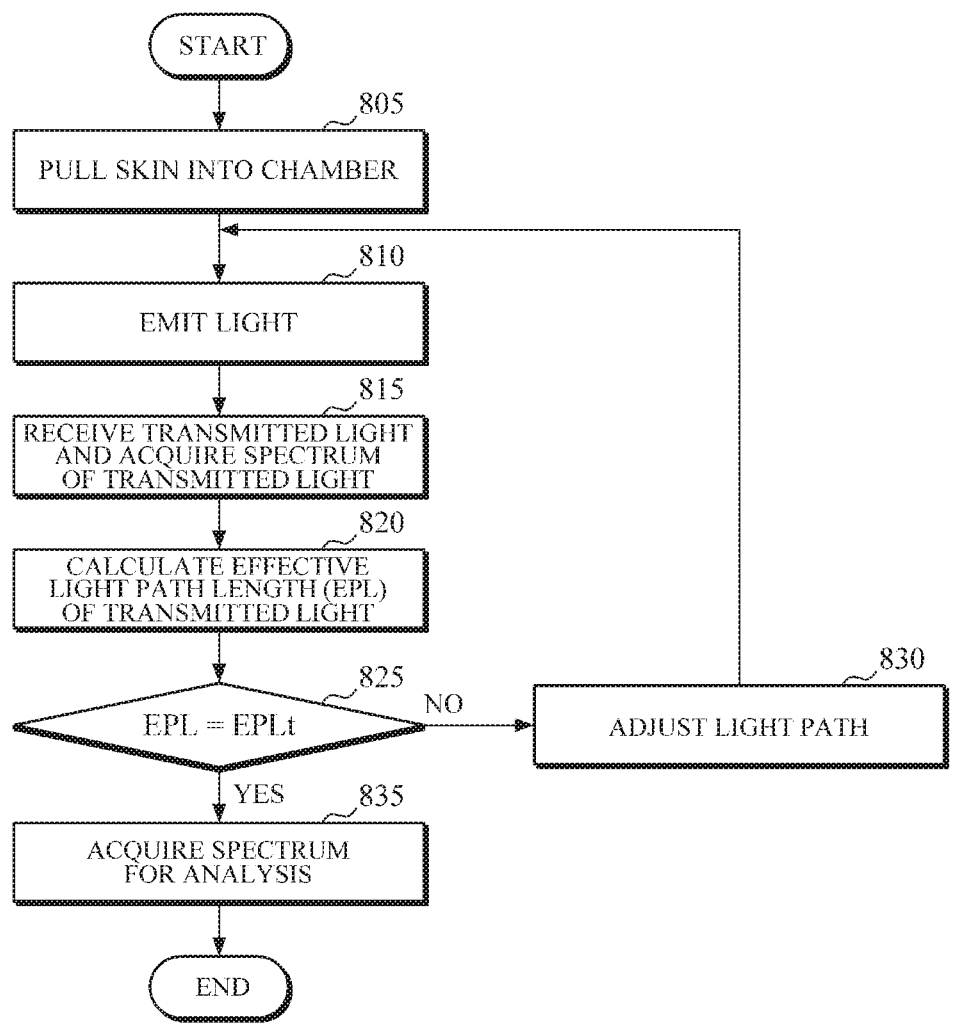
FIG. 8 is a flowchart illustrating an exemplary embodiment of a method of acquiring a spectrum for analysis in a spectrometer.

FIG. 8 is a flowchart illustrating an exemplary embodiment of a method of acquiring a spectrum for analysis in a spectrometer. The method of acquiring a spectrum for analysis of FIG. 8 may be performed by the spectrometer 400 of FIG. 4.

Referring to FIGS. 4 and 8, the spectrometer 400 sucks in the internal air of the chamber 120 so that the skin 10 of the subject is pulled into the chamber 120, in operation 805.

The spectrometer 400 emits light to the skin 10 of the subject, in operation 810. For example, the spectrometer 400 may emit light of a specific wavelength, for example, NIR light to the skin 10. However, the wavelength of the light to be emitted from the spectrometer 400 may vary according to the purpose of measurement or the types of components to be measured.

The spectrometer 400 receives transmitted light passing through the skin 10 and acquires a spectrum of the received light, in operation 815.

The spectrometer 400 calculates an effective light path length (EPL) of the transmitted light, in operation 820. The EPL refers to a length of light passing through the water element of skin of the subject. According to an exemplary embodiment, the spectrometer 400 may calculate the EPL by analyzing the spectrum of the transmitted light using a CLS algorithm. However, this is merely an exemplary embodiment, and aspects of the present disclosure are not limited thereto. That is, the spectrometer 400 may calculate the EPL using various well-known methods.

The spectrometer 400 may determine whether the calculated EPL is identical with a predetermined target effective light path length EPLt, in operation 825, and may adjust the propagation path of light emitted to the skin 10 from the light source 430, in operation 830, when the two effective light path lengths are not the same. For instance, the spectrometer 400 may change the propagation direction of light emitted from the light source 430 by refracting the light at a predetermined angle using the optical device 500, which is described with reference to FIG. 5. Alternatively, the spectrometer 400 may change the propagation direction of light using a reflector capable of adjusting an angle of reflection, a combination of the reflector and the optical device 500, or a driving device capable of operating the reflector (e.g., by changing an angle of reflection of the reflector) or the combination of the reflector and the optical device 500. In addition, the spectrometer 400 may change the propagation path of light using a refraction device having a predetermined angle of refraction and an adjustment device capable of adjusting the refraction device (e.g., by axially rotating the refraction device) to change a direction of refraction by the refraction device.

When the propagation path of the light is adjusted, the spectrometer 400 returns to operation 810 to emit light to the skin 10. That is, the spectrometer 400 repeats the operations 810, 815, 820, 825, and 830 until the EPL and the EPLt are identical with each other.

On the other hand, when it is determined in operation 825 that the EPL of the transmitted light is identical with the EPLt, the spectrometer 400 acquires a spectrum of the transmitted light as a spectrum for analysis, in operation 835.

Figure 9:
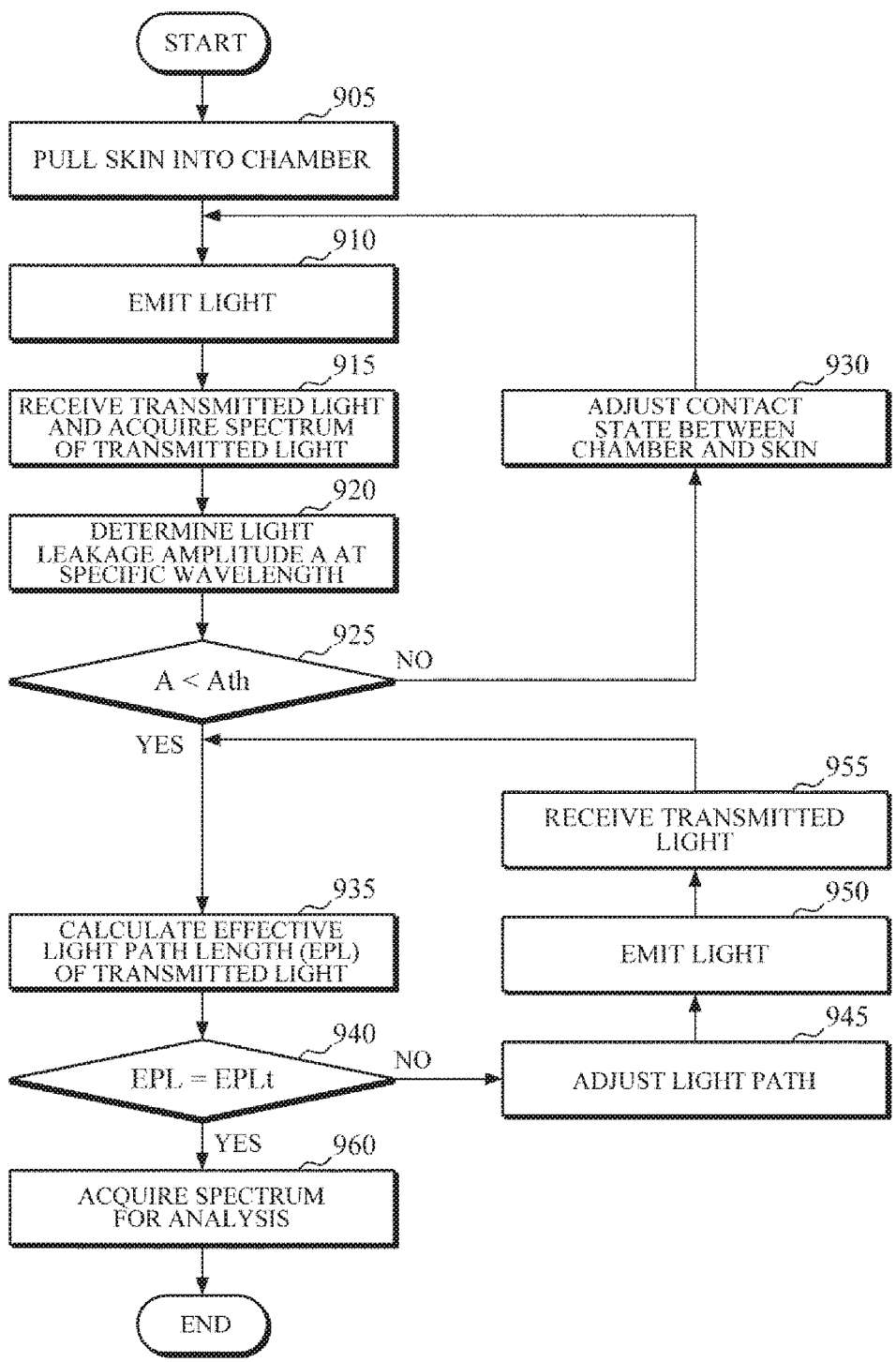
FIG. 9 is a flowchart illustrating another exemplary embodiment of a method of acquiring a spectrum for analysis in a spectrometer.

FIG. 9 is a flowchart illustrating another exemplary embodiment of a method of acquiring a spectrum for analysis in a spectrometer. The method of acquiring a spectrum for analysis of FIG. 9 may be performed by the spectrometer 400 of FIG. 4.

Referring to FIGS. 4 and 9, the spectrometer 400 sucks in the internal air of the chamber 120 so that the skin 10 of the subject is pulled into the chamber 120, in operation 905.

The spectrometer 400 emits light to the skin 10 of the subject, in operation 910. For example, the spectrometer 400 may emit light of a specific wavelength, for example, NIR light, to the skin 10. However, the wavelength of the light to be emitted from the spectrometer 400 may vary according to the purpose of measurement or the types of components to be measured.

The spectrometer 400 receives transmitted light passing through the skin 10 and acquires a spectrum of the received light, in operation 915.

The spectrometer 400 determines light leakage amplitude A at a specific wavelength by analyzing the spectrum of the transmitted light, in operation 920, and compares the light leakage amplitude A with a predetermined threshold Ath, in operation 925. In this case, the specific wavelength may be a wavelength that reacts with water, e.g., a wavelength to be absorbed by water, and may be set variously according to the purpose of measurement or a type of constituent element to be measured.

When it is determined that the light leakage amplitude A at the specific wavelength is equal to or greater than the predetermined threshold Ath, the spectrometer 400 determines that the contact state between the chamber 120 and the skin 10 is inadequate and adjusts the contact state between the chamber 120 and the skin 10, in operation 930. According to an exemplary embodiment, the spectrometer 400 may adjust the contact state between the chamber 120 and the skin 10 by applying a physical force around the skin 10 pulled into the chamber 120. For example, when it is determined that the light leakage amplitude A at the specific wavelength is equal to or greater than the predetermined threshold Ath, the spectrometer 100 may apply a physical force around the skin 10 of the subject pulled into the chamber 120 by vertically pressing the periphery of the skin 10 pulled into the chamber 120 or oscillating back and forth or side to side around the skin 10 pulled into the chamber 120. When the physical force is applied around the skin 10 of the subject pulled into the chamber 120, the process of the chamber 120 and the skin 10 of the subject contacting and separating from each other is repeated, and thereby the contact state between the chamber 120 and the skin 10 may be adjusted.

The spectrometer 400 may adjust the physical force around the skin 10 pulled into the chamber 120 according to the light leakage amplitude at a specific wavelength. For example, the spectrometer 400 may classify the vertical force pressing the periphery of the skin 10 of the subject pulsed into the chamber 120 into a number of levels according to the magnitude of the force, and may divide the force that oscillates back and forth or side to side around the skin 10 of the subject pulled into the chamber 120 into a number of levels according to the magnitude of the force. In addition, the spectrometer 400 may appropriately adjust the magnitude of the force pressing the periphery of the skin 10 of the subject pulled into the chamber 120 and/or the magnitude of the force oscillating back and forth or side to side around the skin 10 of the subject pulled into the chamber 120 by applying the force of a specific level corresponding to the contact state (e.g., light leakage amplitude) between the chamber 120 and the skin 10.

When the contact state between the chamber 120 and the skin 10 is adjusted, the spectrometer 400 returns to operation 910 to emit light to the skin 10. That is, the spectrometer 400 repeats operations 910, 915, 920, 925, and 930 until the light leakage amplitude A at the specific wavelength is less than the predetermined threshold Ath.

When the light leakage amplitude A at the specific wavelength is less than the predetermined threshold Ath, the spectrometer 400 determines that the contact state between the chamber 120 and the skin 10 is adequate and calculates an EPL of the transmitted light, as depicted in 935. According to an exemplary embodiment, the spectrometer 400 may calculate the EPL by analyzing the spectrum of the transmitted light using a CLS algorithm.

The spectrometer 400 may determine whether the calculated EPL is identical with a predetermined target effective light path length EPLt, in operation 940, and may adjust the propagation path of light emitted to the skin 10 from the light source 430, in operation 945, when the two effective light path lengths are not the same. For instance, the spectrometer 400 may change the propagation direction of light emitted from the light source 430 by refracting the light at a predetermined angle using the optical device 500, which is described with reference to FIG. 5. Alternatively, the spectrometer 400 may change the propagation direction of light using a reflector capable of adjusting an angle of reflection, a combination of the reflector and the optical device 500, or a driving device capable of operating the reflector (e.g., by changing an angle of reflection of the reflector) or the combination of the reflector and the optical device 500. In addition, the spectrometer 400 may change the propagation path of light using a refraction device having a predetermined angle of refraction and an adjustment device capable of adjusting the refraction device (e.g., by axially rotating the refraction device) to change a direction of refraction by the refraction device.

When the propagation path of the light is adjusted, the spectrometer 400 again emits light to the skin 10, in operation 950. Then, the spectrometer 400 receives transmitted light passing through the skin 10 and acquires a spectrum of the received light, in operation 955.

Upon completion of receiving the transmitted light and acquiring the spectrum of the transmitted light, the spectrometer 400 returns to operation 935 to calculate an EPL of the transmitted light. That is, the spectrometer 400 repeats the operations 935, 940, 945, 950, and 955 until the EPL of the transmitted light and the predetermined EPLt are identical with each other.

On the other hand, when it is determined in operation 940 that the EPL of the transmitted light is identical with the predetermined EPLt, the spectrometer 400 acquires a spectrum of the transmitted light as a spectrum for analysis, in operation 960.

Figure 10:
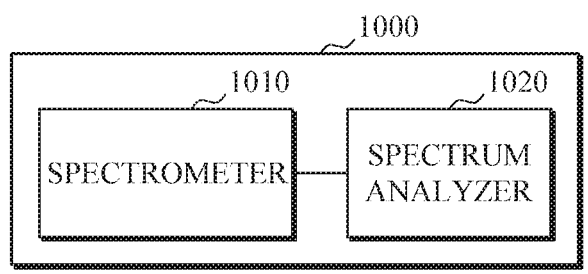
FIG. 10 is a block diagram illustrating an exemplary embodiment of an apparatus for analyzing a biological component.

FIG. 10 is a block diagram illustrating an exemplary embodiment of an apparatus for analyzing a biological component.

The apparatus 1000 for analyzing a biological component may be mounted in an electronic device. In this case, the electronic device may include a mobile phone, a smartphone, a table computer, a notebook computer, a personal digital assistant (PDA), a portable multimedia player (PMP), a navigation system, an MP3 player, a digital camera, a wearable device, and the like, and the wearable device may include a wristwatch type, a wristband type, a ring-type, a belt-type, a necklace-type, an ankle-band type, a thigh-band type, a forearm-band type, or the like. However, the electronic device is not limited to the above examples, and the wearable device is also not limited to the above examples.

Referring to FIG. 10, the apparatus 100 includes a spectrometer 1010 and a spectrum analyzer 1020.

The spectrometer 1010 is a device capable of acquiring a skin spectrum of a subject (e.g., a spectrum of transmitted light passing through the skin of the subject), and may be the same as either of the spectrometers 100 or 400 which are described with reference to FIGS. 1 to 9, and hence detailed description thereof will be omitted.

The spectrum analyzer 1020 analyzes a biological component of the subject, such as a blood sugar, by analyzing the skin spectrum acquired through the spectrometer 1010. In this case, the spectrum analyzer 1020 may analyze the biological component of the subject using various well-known methods.

The current exemplary embodiments can be implemented as computer readable codes in a computer readable recording medium. Codes and code segments constituting the computer program can be easily inferred by a skilled computer programmer in the art. The computer readable recording medium includes all types of recording media in which computer readable data are stored. Examples of the computer readable recording medium include a ROM, a RAM, a CD-ROM, a magnetic tape, a floppy disk, and an optical data storage. Further, the recording medium may be implemented in the form of a carrier wave such as Internet transmission. In addition, the computer readable recording medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A spectrometer comprising:
a chamber;
a vacuum generator configured to suck in internal air of the chamber to pull skin of a subject into the chamber;
a light source configured to emit light to the skin of the subject pulled into the chamber;
a photodetector configured to receive the light that has passed through the skin of the subject and acquire a spectrum of the light; and
a skin contact adjuster configured to determine a contact state between an inner wall of the chamber and the skin pulled into the chamber by analyzing the spectrum of the light and thereby generate a determination result, and adjust the contact state between the inner wall of the chamber and the skin pulled into the chamber from a first contact position to a second contact position by applying a physical force to a region of the skin of the subject immediately surrounding the skin pulled into the chamber according to the determination result,
wherein the skin contact adjuster is configured to adjust the contact state between the inner wall of the chamber and the skin pulled into the chamber without adjusting an amount of the internal air of the chamber,
wherein the skin contact adjuster is configured to apply the physical force to the region of the skin by oscillating back and forth or side to side around the skin pulled into the chamber.

2. The spectrometer of claim 1, wherein the skin contact adjuster is configured to determine light leakage amplitude at a specific wavelength based on the spectrum of the light and determine the contact state between the chamber and the skin based on the light leakage amplitude at the specific wavelength.

3. The spectrometer of claim 2, wherein the skin contact adjuster is configured to determine that the contact state between the chamber and the skin is inadequate, in response to the light leakage amplitude at the specific wavelength being equal to or greater than a predetermined threshold, and adjust the contact state between the chamber and the skin by applying the physical force to the region of the skin.

4. The spectrometer of claim 1, wherein the skin contact adjuster is configured to adjust the physical force applied to the region of the skin according to light leakage amplitude at a specific wavelength which is determined based on the spectrum of the light.

5. The spectrometer of claim 1, further comprising a light path adjuster configured to calculate an effective light path length of the light and adjust a propagation path of the light to be emitted to the skin from the light source based on the calculated effective light path length.

6. The spectrometer of claim 5, wherein the light path adjuster is configured to calculate the effective light path length by analyzing the spectrum of the light using a classical least square (CLS) algorithm.

7. The spectrometer of claim 5, wherein the light path adjuster is configured to adjust the propagation path of the light using two liquids which form a continuous refractive interface and are not mixed with each other.

8. The spectrometer of claim 5, wherein the light path adjuster comprises:
    a container;
    two liquids inside of the container which form an interface with each other and are not mixed with each other; and
    a plurality of electrodes which induce an electric field of a predetermined magnitude inside the container so that a direction of the interface is changed.

9. The spectrometer of claim 8, wherein one of the two liquids is a conductive liquid and the other liquid is an insulating liquid.

10. A method of operating a spectrometer, the method comprising:
    pulling skin of a subject into a chamber by sucking in internal air of the chamber;
    emitting light to the skin of the subject pulled into the chamber;
    receiving the light passing through the skin of the subject and acquiring a spectrum of the light;
    determining a contact state between an inner wall of the chamber and the skin pulled into the chamber by analyzing the spectrum of the light and thereby generating a determination result; and
    adjusting the contact state between the chamber and the skin, without adjusting an amount of the internal air of the chamber, by applying a physical force to a region of the skin of the subject immediately surrounding the skin pulled into the chamber according to the determination result,
    wherein the skin of the subject remains pulled into the chamber after the adjusting of the contact state, and
    wherein the physical force is applied to the region of the skin by oscillating back and forth or side to side around the skin pulled into the chamber.

11. The method of claim 10, wherein the determining of the contact state between the chamber and the skin comprises determining light leakage amplitude at a specific wavelength based on the spectrum of the light and determining the contact state between the chamber and the skin based on the light leakage amplitude at the specific wavelength.

12. The method of claim 11, wherein the determining of the contact state between the chamber and the skin comprises determining that the contact state between the chamber and the skin is inadequate, in response to the light leakage amplitude at the specific wavelength being equal to or greater than a predetermined threshold.

13. The method of claim 10, wherein the adjusting of the contact state between the chamber and the skin comprises adjusting the physical force around the skin pulled into the chamber according to light leakage amplitude at a specific wavelength which is determined based on the spectrum of the light.

14. The method of claim 10, further comprising:
    calculating an effective light path length of the light; and
    adjusting a propagation path of the light to be emitted to the skin from a light source based on the calculated effective light path length.

15. The method of claim 14, wherein the calculating of the effective light path length of the light comprises calculating the effective light path length by analyzing the spectrum of the light using a classical least square (CLS) algorithm.

16. The method of claim 14, wherein the adjusting of the propagation path of the light comprises adjusting the propagation path of the light using two liquids which form a continuous refractive interface and are not mixed with each other.

17. The method of claim 16, wherein one of the two liquids is a conductive liquid and the other liquid is an insulating liquid.

* * * * *